United States Patent [19]

Skaletzky

[11] Patent Number: 4,474,791
[45] Date of Patent: Oct. 2, 1984

[54] DIURETIC 2,6-DIARYL-4-PYRIDINE CARBOXYLIC ACIDS

[75] Inventor: Louis L. Skaletzky, Kalamazoo, Mich.

[73] Assignee: The Upjohn Company, Kalamazoo, Mich.

[21] Appl. No.: 449,101

[22] Filed: Dec. 13, 1982

Related U.S. Application Data

[62] Division of Ser. No. 259,135, Apr. 30, 1982, Pat. No. 4,377,586.

[51] Int. Cl.$^3$ .................. A61K 31/455; C07D 213/55; C07D 409/02; C07D 409/12
[52] U.S. Cl. ..................................... 424/266; 546/326; 546/284
[58] Field of Search ................. 546/326, 284; 424/266

[56] References Cited

U.S. PATENT DOCUMENTS 3,600,396  8/1971  Ash et al. ............................ 546/334
3,753,997  8/1973  Ash et al. ............................ 546/194
3,763,148  10/1973 Ash et al. ............................ 546/326
3,764,604  10/1973 Ash et al. ............................ 546/133

OTHER PUBLICATIONS

Blumbergs, P. et al., Antimalarials, 2, 2,6—Bis(aryl-)—4—pyridinemethanols, 1972, p. 808.
Markovac, A. et al., Antimalarials, 3, 2,6—Bis(aryl-)—4—pyridinemethanols, 1972, p. 918.
La Montagne, M. P. et al., Antimalarials, 5, 2—aryl—6—trifluoromethyl—4—pyridine methanols, 1973, p. 1040.

*Primary Examiner*—Henry R. Jiles
*Assistant Examiner*—Dale A. Bjorkman
*Attorney, Agent, or Firm*—Lawrence T. Welch

[57] ABSTRACT

The present invention provides novel methods of inducing diuresis and/or an antihypertensive effect employing certain 2,6-diaryl-4-pyridinecarboxylic acid derivatives. Also provided are novel compositions to be used in these methods.

10 Claims, No Drawings

DIURETIC 2,6-DIARYL-4-PYRIDINE CARBOXYLIC ACIDS

DESCRIPTION

CROSS REFERENCE TO RELATED APPLICATIONS

This application is a division of copending application Ser. No. 259,135, filed Apr. 30, 1982, issued as U.S. Pat. No. 4,377,586.

BACKGROUND OF THE INVENTION

The present invention relates to the use of certain 2,6-diaryl-4-pyridine carboxylic acids to induce diuresis and hypertension and provides certain novel compositions for this purpose. The preparation and use of these compounds and compositions is described in U.S. Pat. No. 4,377,586, which is expressly incorporated herein by reference.

PRIOR ART

Many classes of diuretics are known. See, e.g., Goth, Med. Pharma. 9th Ed. (1978); and Goodman and Gillman, The Pharmacological Basis of therapeutics, 5th ed. (1971). 2,6-Diaryl-4-pyridinecarboxylic acids are disclosed as intermediates for anti-malarial compounds in U.S. Pat. Nos. 3,753,997; 3,763,148; 3,764,604; and 3,600,396 and J. Med. Chem., 15:918–922 (1972); J. Med. Chem. 16:1040–1041 (1973); and J. Med. Chem., 15:808–812 (1972).

SUMMARY OF THE INVENTION

The present invention provides
(1) a method for inducing diuresis in a human which comprises administering to said human an amount effective to cause diuresis of a compound of the Formula IIA,
wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, bromo, iodo, methyl, or trifluoromethyl;
(5) $X_{30}$ is phenyl, p-fluorophenyl, phenoxy, p-fluorophenoxy, or thiophenoxy;
(6) $X_{40}$ is hydrogen, chloro, fluoro, trifluoromethyl, or methyl; or
(7) $X_{30}$ and $X_{40}$ when taken together with the phenyl moiety to which they are attached form 2-naphthalenyl, 5,6,7,8-tetrahydro-2-napthalenyl, or 6-chloro-2-naphthalenyl; and
with the following provisos:
(a) at least one of $X_{10}$ and $X_{20}$ is other than hydrogen;
(b) $X_{20}$ is methyl only when $X_{30}$ and $X_{40}$ form 2-naphthalenyl;
(c) $X_{30}$ is thiophenoxy only when $X_{10}$ and $X_{40}$ are hydrogen; and
(d) $X_{40}$ is fluoro only when $X_{30}$ is phenyl;
(2) a compound of the Formula III,
wherein
(1) $R_{10}$ is hydrogen or methyl;
(2) $R_{20}$ is hydrogen or a pharmacologically acceptable cation;
(3) $X_{21}$ is chloro, fluoro, bromo, iodo, methyl, or trifluoromethyl;
(4) $X_{31}$ is hydrogen, methyl, chloro, bromo, iodo, trifluoromethyl, phenyl, p-fluorophenyl, phenoxy, p-fluorophenoxy, thiophenoxy, or —CH$_2$R$_{50}$ wherein R$_{50}$ is (C$_2$–C$_7$) alkyl;
(5) $X_{41}$ is hydrogen, chloro, fluoro, trifluoromethyl, or methyl; or
(6) $X_{31}$ and $X_{41}$ when taken together with the phenyl moiety to which they are attached form 2-naphthalenyl or 5,6,7,8-tetrahydro-2-naphthalenyl, or 6-chloro-2-naphthalenyl;
(7) $X_{50}$ is hydrogen (C$_1$–C$_4$) alkoxy or acetoxy;
with the following provisos:
(a) at least one of $X_{31}$ and $X_{41}$ is other than hydrogen;
(b) one of $X_{31}$ and $X_{41}$ is methyl only when the other is methyl;
(c) $X_{21}$ and $X_{31}$ are chloro, bromo, or trifluoromethyl (being the same or different) only when $R_{10}$ or $X_{50}$ is other than hydrogen;
(d) $X_{21}$ is chloro only when $X_{41}$ is not chloro;
(e) $X_{21}$ is methyl only when $X_{31}$ and $X_{41}$ form 2-naphthalenyl;
(f) $X_{50}$ is (C$_1$–C$_4$) alkoxy or acetoxy only when $X_{41}$ is hydrogen, $X_{21}$ is chloro, bromo, iodo, or trifluoromethyl, and $X_{31}$ is chloro, bromo, iodo, trifluoromethyl or CH$_2$R$_{50}$;
(g) $X_{21}$ is fluoro only when $R_{10}$ is methyl and $X_{31}$ is chloro;
(h) $X_{31}$ is thiophenoxy only when $X_{41}$ and $X_{50}$ are hydrogen; and
(i) $X_{41}$ is fluoro only when $X_{31}$ is phenyl;
(3) a pharmaceutical composition comprising:
(a) a compound of the formula II,
wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, fluoro, bromo, iodo, methyl, or trifluoromethyl;
(5) $X_{30}$ is hydrogen, methyl, chloro, bromo, iodo, trifluoromethyl, phenyl, p-fluorophenyl, phenoxy, p-fluorophenoxy, thiophenoxy, or —CH$_2$—R$_{50}$, wherein R$_{50}$ is (C$_2$–C$_7$) alkyl; or
(6) $X_{40}$ is hydrogen, chloro, fluoro, trifluoromethyl, or methyl; or
(7) $X_{30}$ and $X_{40}$ when taken together with the phenyl moiety to which they are attached form 2-naphthalenyl 5,6,7,8-tetrahydro-2-napthalenyl, or 6-chloro-2-naphthalenyl; and
(8) $X_{50}$ is hydrogen, (C$_1$–C$_4$) alkoxy or acetoxy;
with the following provisos:
(a) at least one of $X_{10}$ and $X_{20}$ and at least one of $X_{30}$ and $X_{40}$ is other than hydrogen;
(b) $X_{10}$ is trifluoromethyl only when $X_{20}$ is hydrogen, $X_{30}$ is hydrogen, and $X_{40}$ is trifluoromethyl;
(c) $X_{40}$ is chloro only when $X_{30}$ is chloro;
(d) one of $X_{30}$ and $X_{40}$ is methyl only when the other is methyl;
(e) $X_{20}$ is methyl only when $X_{30}$ and $X_{40}$ form 2-naphthalenyl;
(f) $X_{50}$ is (C$_1$–C$_4$) alkoxy or acetoxy only when $X_{10}$ and $X_{40}$ are hydrogen, $X_{20}$ is chloro, bromo, iodo, or trifluoromethyl, and $X_{30}$ is chloro, bromo, iodo, trifluoromethyl, or CH$_2$—R$_{50}$;
(g) $X_{20}$ is fluoro only when $R_{10}$ is methyl and $X_{30}$ is chloro;
(h) $X_{30}$ is thiophenoxy only when $X_{10}$, $X_{40}$, and $X_{50}$ are hydrogen; and
(i) $X_{40}$ is fluoro only when $X_{30}$ is phenyl; and (b) a pharmaceutical excipient;
(4) a method for producing an antihypertensive effect in a human which comprises concomittantly administering to said human
(a) an amount effective to induce diuresis of a compound of the formula II
wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, fluoro, bromo, iodo, methyl, or trifluoromethyl;
(5) $X_{30}$ is hydrogen, methyl, chloro, bromo, iodo, trifluoromethyl, phenyl, p-fluorophenyl, phenoxy, p-fluorophenoxy, thiophenoxy, or —$CH_2$—$R_{50}$, wherein $R_{50}$ is ($C_2$-$C_7$) alkyl; or
(6) $X_{40}$ is hydrogen, chloro, fluoro, trifluoromethyl, or methyl; or
(7) $X_{30}$ and $X_{40}$ when taken together with the phenyl moiety to which they are attached form 2-naphthalenyl 5,6,7,8-tetrahydro-2-napthalenyl, or 6-chloro-2-naphthalenyl; and
(8) $X_{50}$ is hydrogen, ($C_1$-$C_4$) alkoxy or acetoxy; with the following provisos:
  (a) at least one of $X_{10}$ and $X_{20}$ and at least one of $X_{30}$ and $X_{40}$ is other than hydrogen;
  (b) $X_{10}$ is trifluoromethyl only when $X_{20}$ is hydrogen, $X_{30}$ is hydrogen, and $X_{40}$ is trifluoromethyl;
  (c) $X_{40}$ is chloro only when $X_{30}$ is chloro;
  (d) one of $X_{30}$ and $X_{40}$ is methyl only when the other is methyl;
  (e) $X_{20}$ is methyl only when $X_{30}$ and $X_{40}$ form 2-naphthalenyl;
  (f) $X_{50}$ is ($C_1$-$C_4$) alkoxy or acetoxy only when $X_{10}$ and $X_{40}$ are hydrogen, $X_{20}$ is chloro, bromo, iodo, or trifluoromethyl, and $X_{30}$ is chloro, bromo, iodo, trifluoromethyl, or $CH_2$—$R_{50}$;
  (g) $X_{20}$ is fluoro only when $R_{10}$ is methyl and $X_{30}$ is chloro;
  (h) $X_{30}$ is thiophenoxy only when $X_{10}$, $X_{40}$, and $X_{50}$ are hydrogen; and
  (i) $X_{40}$ is fluoro only when $X_{30}$ is phenyl; and
  (b) an antihypertensive agent; and
(5) a pharmaceutical composition comprising:
(a) a compound of the formula II;
wherein
(1) $R_{10}$ is hydrogen or methyl;
(2) $R_{20}$ is hydrogen or a pharmacologically acceptable cation;
(3) $X_{10}$ is hydrogen or trifluoromethyl;
(4) $X_{20}$ is hydrogen, chloro, fluoro, bromo, iodo, methyl, or trifluoromethyl;
(5) $X_{30}$ is hydrogen, methyl, chloro, bromo, iodo, trifluoromethyl, phenyl, p-fluorophenyl, phenoxy, p-fluorophenoxy, thiophenoxy, or —$CH_2$—$R_{50}$, wherein $R_{50}$ is ($C_2$-$C_7$) alkyl; or
(6) $X_{40}$ is hydrogen, chloro, fluoro, trifluoromethyl, or methyl; or
(7) $X_{30}$ and $X_{40}$ when taken together with the phenyl moiety to which they are attached form 2-naphthalenyl 5,6,7,8-tetrahydro-2-napthalenyl, or 6-chloro-2-naphthalenyl; and
(8) $X_{50}$ is hydrogen, ($C_1$-$C_4$) alkoxy or acetoxy; with the following provisos:
  (a) at least one of $X_{10}$ and $X_{20}$ and at least one of $X_{30}$ and $X_{40}$ is other than hydrogen;
  (b) $X_{10}$ is trifluoromethyl only when $X_{20}$ is hydrogen, $X_{30}$ is hydrogen, and $X_{40}$ is trifluoromethyl;
  (c) $X_{40}$ is chloro only when $X_{30}$ is chloro;
  (d) one of $X_{30}$ and $X_{40}$ is methyl only when the other is methyl;
  (e) $X_{20}$ is methyl only when $X_{30}$ and $X_{40}$ form 2-naphthalenyl;
  (f) $X_{50}$ is ($C_1$-$C_4$) alkoxy or acetoxy only when $X_{10}$ and $X_{40}$ are hydrogen, $X_{20}$ is chloro, bromo, iodo, or trifluoromethyl, and $X_{30}$ is chloro, bromo, iodo, trifluoromethyl, or $CH_2$—$R_{50}$;
  (g) $X_{20}$ is fluoro only when $R_{10}$ is methyl and $X_{30}$ is chloro;
  (h) $X_{30}$ is thiophenoxy only when $X_{10}$, $X_{40}$, and $X_{50}$ are hydrogen; and
  (i) $X_{40}$ is fluoro only when $X_{30}$ is phenyl; and
  (b) an antihypertensive agent; and
  (c) a pharmaceutical excipient.

DESCRIPTION OF THE PREFERRED EMBODIMENTS

Preferred embodiments of the present invention include:
(1) a method of inducing diuresis employing a compound selected from the group consisting of;
[2-[1,1'-biphenyl]-4-yl-6-(4-chlorophenyl)-4-pyridinecarboxylic acid,
2-(4-methylphenyl)-6-(2-naphthalenyl)-4-pyridinecarboxylic acid,
2-(4-chlorophenyl)-6-(5,6,7,8-tetrahydro-2-naphthalenyl)-4-pyridinecarboxylic acid,
2-(4-chloro-2-methoxyphenyl)-6-(4-chlorophenyl)-4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(1,1'-biphenyl)-4-yl-6-(4-bromophenyl)-4-pyridinecarboxylic acid, and
2-(4-bromophenyl)-6-(2-naphthalenyl)-4-pyridinecarboxylic acid.
(2) novel compounds selected from the group consisting of;
2-(4-chlorophenyl)-6-[3-(trifluoromethyl)phenyl]-4-pyridinecarboxylic acid,
2-(4-bromophenyl)-6-[3-(trifluoromethyl)phenyl]-4-pyridinecarboxylic acid,
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(3,4-dimethylphenyl)-4-pyridinecarboxylic acid,
2,6-bis(4-chlorophenyl)-3-methyl-4-pyridinecarboxylic acid,
2-(4-chlorophenyl)-6-(4-iodophenyl)-4-pyridinecarboxylic acid,
2-(4-chlorophenyl)-6-(4-propylphenyl)-4-pyridinecarboxylic acid,
2-(4-chlorophenyl)-6-(4-phenoxyphenyl-4-pyridinecarboxylic acid, 2-(4-chlorophenyl)-6-[4-(2-phenylthio)phenyl]-4-pyridinecarboxylic acid,
2-(4-chlorophenyl)-6-[4-(2-methylpropyl)phenyl]-4-pyridinecarboxylic acid,
2-(4-methylphenyl)-6-(2-naphthalenyl)-4-pyridinecarboxylic acid,
2-(4-butylphenyl)-6-(4-chlorophenyl)-4-pyridinecarboxylic acid,
2-(4-chlorophenyl)-6-(5,6,7,8-tetrahydro-2-naphthalenyl)-4-pyridinecarboxylic acid,
2-(4-chlorophenyl)-6-[4-(3-methylbutyl)phenyl]-4-pyridinecarboxylic acid,
2-(4-chloro-2-methoxyphenyl)-6-(4-chlorophenyl)-4-pyridine carboxylic acid,
2-[2-(acetyloxy)-4-chlorophenyl]-6-(4-chlorophenyl)-4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(4-chlorophenyl)-6-(4-fluorophenyl)-3-methyl-4-pyridinecarboxylic acid,
2-(1,1'-biphenyl)-4-yl-6-(4-bromophenyl)-4-pyridinecarboxylic acid,
2-(4-bromophenyl)-6-(2-naphthalenyl)-4-pyridinecarboxylic acid,
2-(4-bromophenyl)-6-(4-chlorophenyl)-5-methyl-4-pyridinecarboxylic acid,
2,6-bis[(3-trifluoromethyl)phenyl]-4-pyridinecarboxylic acid, and
2-(4-bromophenyl)-6-(4-chlorophenyl)-4-pyridine carboxylic acid;

(3) a method for inducing an antihypertensive effect employing a compound selected from the group consisting of:
2-(4-chlorophenyl)-6-[3-(trifluoromethyl)phenyl]-4-pyridinecarboxylic acid,
2-(4-bromophenyl)-6-[3-(trifluoromethyl)phenyl]-4-pyridinecarboxylic acid,
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(3,4-dimethylphenyl)-4-pyridinecarboxylic acid,
2,6-bis(4-chlorophenyl)-3-methyl-4-pyridinecarboxylic acid,
2-(4-chlorophenyl)-6-(4-iodophenyl)-4-pyridinecarboxylic acid,
2-(4-chlorophenyl)-6-(4-propylphenyl)-4-pyridinecarboxylic acid,
2-(4-chlorophenyl)-6-(4-phenoxyphenyl-4-pyridinecarboxylic acid,
2-(4-chlorophenyl)-6-[4-(phenylthio)phenyl]-4-pyridine-carboxylic acid,
2-(4-chlorophenyl)-6-[4-(2-methylpropyl)phenyl]-4-pyridinecarboxylic acid,
2-(4-methylphenyl)-6-(2-naphthalenyl)-4-pyridinecarboxylic acid,
2-(4-butylphenyl)-6-(4-chlorophenyl)-4-pyridinecarboxylic acid,
2-(4-chlorophenyl)-6-(5,6,7,8-tetrahydro-2-naphthalenyl)-4-pyridinecarboxylic acid,
2-(4-chlorophenyl)-6-[4-(3-methylbutyl)phenyl]-4-pyridinecarboxylic acid,
2-(4-chloro-2-methoxyphenyl)-6-(4-chlorophenyl)-4-pyridinecarboxylic acid,
2-[2-(acetyloxy)-4-chlorophenyl]-6-(4-chlorophenyl)-4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(4-chlorophenyl)-6-(4-fluorophenyl)-3-methyl-4-pyridinecarboxylic acid,
2-(1,1'-biphenyl)-4-yl-6-(4-bromophenyl)-4-pyridinecarboxylic acid,
2-(4-bromophenyl)-6-(2-naphthalenyl)-4-pyridinecarboxylic acid,
2-(4-bromophenyl)-6-(4-chlorophenyl)-5-methyl-4-pyridinecarboxylic acid,
2,6-bis(4-chlorophenyl)-4-pyridinecarboxylic acid,
2,6-bis(4-chlorophenyl)-4-pyridine carboxylic acid, sodium salt hydrate,
2,6-bis[(3-trifluoromethyl)phenyl]-4-pyridinecarboxylic acid,
2-(4-bromophenyl)-6-(4-chlorophenyl)-4-pyridine carboxylic acid,
1-(4-chlorophenyl)-6-[4-(trifluoromethyl)phenyl]-4-pyridinecarboxylic acid,
2,6-bis[4-(trifluoromethyl)-phenyl]-4-pyridine carboxylic acid,
2,6-bis(4-bromophenyl)-4-pyridine carboxylic acid,
2-(4-chlorophenyl)-6-(3,4-dichlorophenyl)-4-pyridinecarboxylic acid, and
2,6-Bis(4-chlorophenyl)-3-methyl-4-pyridinecarboxylic acid; and (4) novel pharmaceutical compositions containing a compound selected from the group consisting of
2-(4-chlorophenyl)-6-[3-(trifluoromethyl)phenyl]-4-pyridinecarboxylic acid,
2-(4-bromophenyl)-6-[3-(trifluoromethyl)phenyl]-4-pyridinecarboxylic acid,
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(3,4-dimethylphenyl)-4-pyridinecarboxylic acid,
2,6-bis(4-chlorophenyl)-3-methyl-4-pyridinecarboxylic acid,
2-(4-chlorophenyl)-6-(4-iodophenyl)-4-pyridinecarboxylic acid,
2-(4-chlorophenyl)-6-(4-propylphenyl)-4-pyridinecarboxylic acid,
2-(4-chlorophenyl)-6-(4-phenoxyphenyl)-4-pyridinecarboxylic acid,
2-(4-chlorophenyl)-6-[4-(2-phenylthio)phenyl]-4-pyridinecarboxylic acid,
2-(4-chlorophenyl)-6-[4-(2-methylpropyl)phenyl]-4-pyridinecarboxylic acid,
2-(4-methylphenyl)-6-(2-naphthalenyl)-4-pyridinecarboxylic acid, 2-(4-butylphenyl)-6-(4-chlorophenyl)-4-pyridinecarboxylic acid,
2-(4-chlorophenyl)-6-(5,6,7,8-tetrahydro-2-naphthalenyl)-4-pyridinecarboxylic acid,
2-(4-chlorophenyl)-6-[4-(3-methylbutyl)phenyl]-4-pyridinecarboxylic acid,
2-(4-chloro-2-methoxyphenyl)-6-(4-chlorophenyl)-4-pyridinecarboxylic acid,
2-[2-(acetyloxy)-4-chlorophenyl]-6-(4-chlorophenyl)-4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(4-chlorophenyl)-6-(4-fluorophenyl)-3-methyl-4-pyridinecarboxylic acid,
2-(1,1'-biphenyl)-4-yl-6-(4-bromophenyl)-4-pyridinecarboxylic acid,
2-(4-bromophenyl)-6-(2-naphthalenyl)-4-pyridinecarboxylic acid,
2-(4-bromophenyl)-6-(4-chlorophenyl)-5-methyl-4-pyridinecarboxylic acid,
2,6-bis(4-chlorophenyl)-4-pyridinecarboxylic acid,
2,6-bis(4-chlorophenyl)-4-pyridine carboxylic acid, sodium salt hydrate,
2,6-bis([(3-trifluoromethyl)phenyl]-4-pyridinecarboxylic acid,
2-(4-bromophenyl)-6-(4-chlorophenyl)-4-pyridine carboxylic acid,
1-(4-chlorophenyl)-6-[4-(trifluoromethyl)phenyl]-4-pyridinecarboxylic acid,
2,6-bis[4-(trifluoromethyl)-phenyl]-4-pyridine carboxylic acid,
2,6-bis(4-bromophenyl)-4-pyridine carboxylic acid,
2-(4-chlorophenyl)-6-(3,4-dichlorophenyl)-4-pyridinecarboxylic acid, and
2,6-Bis(4-chlorophenyl)-3-methyl-4-pyridinecarboxylic acid.

I claim:
1. A method for inducing diuresis in a human which comprises administering to said human an amount effective to cause diuresis of a compound of the Formula IIA,

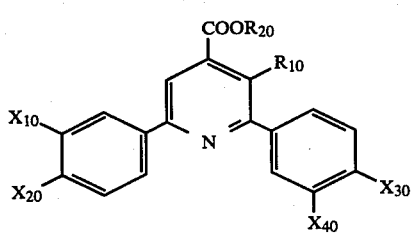

wherein
(1) R₁₀ is hydrogen or methyl;
(2) R₂₀ is hydrogen or a pharmacologically acceptable cation;
(3) X₁₀ is hydrogen or trifluoromethyl;
(4) X₂₀ is hydrogen, chloro, bromo, iodo, methyl, or trifluoromethyl;
(5) X₃₀ is phenyl, p-fluorophenyl, phenoxy, p-fluorophenoxy, or thiophenoxy;
(6) X₄₀ is hydrogen, chloro, fluoro, trifluoromethyl, or methyl; or
(7) X₃₀ and X₄₀ when taken together with the phenyl moiety to which they are attached form 2-naphthenyl, or 6-chloro-2-naphthalenyl;
with the following provisos:
(a) at least one of X₁₀ and X₂₀ is other than hydrogen;
(b) X₂₀ is methyl only when X₃₀ and X₄₀ form 2-naphthalenyl;
(c) X₃₀ is thiophenoxy only when X₁₀ and X₄₀ are hydrogen; and
(d) X₄₀ is fluoro only when X₃₀ is phenyl.

2. A compound of the Formula III,

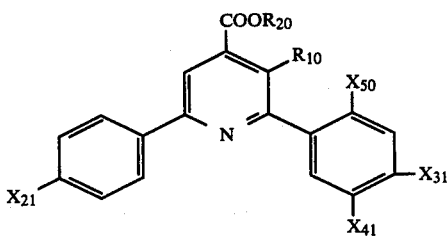

wherein
(1) R₁₀ is hydrogen or methyl;
(2) R₂₀ is hydrogen or a pharmacologically acceptable cation;
(3) X₂₁ is chloro, fluoro, bromo, iodo, methyl, or trifluoromethyl;
(4) X₃₁ is phenyl, p-fluorophenyl, phenoxy, p-fluorophenoxy, or thiophenoxy;
(5) X₄₁ is hydrogen, chloro, fluoro, trifluoromethyl, or methyl; or
(6) X₃₁ and X₄₁ when taken together with the phenyl moiety to which they are attached form 2-naphthalenyl or 6-chloro-2-naphthalenyl;
(7) X₅₀ is hydrogen (C₁–C₄) alkoxy or acetoxy;
with the following provisos:
(a) X₂₁ is chloro only when X₄₁ is not chloro;
(b) X₂₁ is methyl only when X₃₁ and X₄₁ form 2-naphthalenyl;
(c) X₃₁ is thiophenoxy only when X₄₁ and X₅₀ are hydrogen; and
(d) X₄₁ is fluoro only when X₃₁ is phenyl.

3. A diuretic composition consisting of:
(a) a diuretically effective amount of a compound of the formula II,

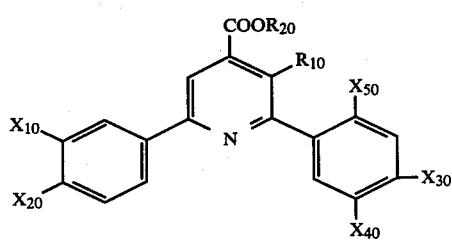

wherein
(1) R₁₀ is hydrogen or methyl;
(2) R₂₀ is hydrogen or a pharmacologically acceptable cation;
(3) X₁₀ is hydrogen or trifluoromethyl;

(4) $X_{20}$ is hydrogen, chloro, fluoro, bromo, iodo, methyl, or trifluoromethyl;

(5) $X_{30}$ is phenyl, p-fluorophenyl, phenoxy, p-fluorophenoxy, or thiophenoxy;

(6) $X_{40}$ is hydrogen, chloro, fluoro, trifluoromethyl, or methyl; or (7) $X_{30}$ and $X_{40}$ when taken together with the phenyl moiety to which they are attached form 2-naphthalenyl or 6-chloro-2-naphthalenyl; and (8) $X_{50}$ is hydrogen, $(C_1-C_4)$ alkoxy or acetoxy; with the following provisos:

(a) at least one of $X_{10}$ and $X_{20}$ and at least one of $X_{30}$ and $X_{40}$ is other than hydrogen;

(b) $X_{20}$ is methyl only when $X_{30}$ and $X_{40}$ form 2-naphthalenyl;

(c) $X_{30}$ is thiophenoxy only when $X_{10}$, $X_{40}$, $X_{50}$ are hydrogen; and (d) $X_{40}$ is fluoro only when $X_{30}$ is phenyl; and (b) a pharmaceutical excipient.

4. A method for producing an antihypertensive effect in a human which comprises concomittantly administering to said human (a) an amount effective to induce diuresis of a compound of the formula II

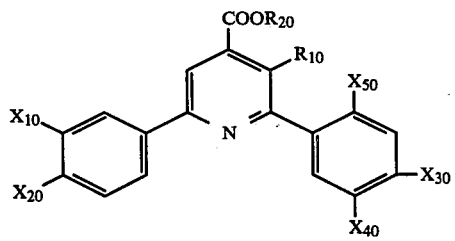

II wherein (1) $R_{10}$ is hydrogen or methyl;

(2) $R_{20}$ is hydrogen or a pharmacologically acceptable cation;

(3) $X_{10}$ is hydrogen or trifluoromethyl;

(4) $X_{20}$ is hydrogen, chloro, fluoro, bromo, iodo, methyl, or trifluoromethyl;

(5) $X_{30}$ is phenyl, p-fluorophenyl, phenoxy, p-fluorophenoxy, or thiophenoxy;

(6) $X_{40}$ is hydrogen, chloro, fluoro, trifluoromethyl, or methyl; or (7) $X_{30}$ and $X_{40}$ when taken together with the phenyl moiety to which they are attached form 2-naphthalenyl or 6-chloro-2-naphthalenyl; and (8) $X_{50}$ is hydrogen, $(C_1-C_4)$ alkoxy or acetoxy; with the following provisos:

(a) at least one of $X_{10}$ and $X_{20}$ and at least one of $X_{30}$ and $X_{40}$ is other than hydrogen;

(b) $X_{20}$ is methyl only when $X_{30}$ and $X_{40}$ form 2-nahthalenyl;

(c) $X_{30}$ is thiophenoxy only when $X_{10}$, $X_{40}$, and $X_{50}$ are hydrogen; and (d) $X_{40}$ is fluoro only when $X_{30}$ is phenyl; and (b) an antihypertensive agent.

5. An antihypertensive composition consisting of:

(a) a diuretically effective amount of a compound of the formula II;

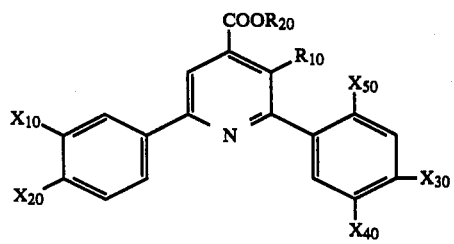

II wherein (1) $R_{10}$ is hydrogen or methyl;

(2) $R_{20}$ is hydrogen or a pharmacologically acceptable cation;

(3) $X_{10}$ is hydrogen or trifluoromethyl;

(4) $X_{20}$ is hydrogen, chloro, fluoro, bromo, iodo, methyl, or trifluoromethyl;

(5) $X_{30}$ is phenyl, p-fluorophenyl, phenoxy, p-fluorophenoxy, or thiophenoxy;

(6) $X_{40}$ is hydrogen, chloro, fluoro, trifluoromethyl, or methyl; or (7) $X_{30}$ and $X_{40}$ when taken together with the phenyl moiety to which they are attached form 2-naphthalenyl or 6-chloro-2-naphthalenyl; and (8) $X_{50}$ is hydrogen, $(C_1-C_4)$ alkoxy or acetoxy; with the following provisos:

(a) at least one of $X_{10}$ and $X_{20}$ and at least one of $X_{30}$ and $X_{40}$ is other than hydrogen;

(b) $X_{20}$ is methyl only when $X_{30}$ and $X_{40}$ form 2-naphthalenyl;

(c) $X_{30}$ is thiophenoxy only when $X_{10}$, $X_{40}$, and $X_{50}$ are hydrogen; and (d) $X_{40}$ is fluoro only when $X_{30}$ is phenyl;

(b) an antihypertensive agent; and (c) a pharmaceutical excipient.

6. A method of claim 1 wherein the compound of the Formula IIA is selected from the group consisting of 2-[1,1'-biphenyl]-4-yl-6-(4-chlorophenyl)-4-pyridinecarboxylic acid, 2-(4-methylphenyl)-6-(2-naphthalenyl)-4-pyridinecarboxylic acid, 2-(4-chlorophenyl)-6-(4'-fluoro-[1,1'-biphenyl]-4-yl)-4-pyridinecarboxylic acid, 2-(4-chlorophenyl)-6-(2-fluoro-[1,1'-biphenyl]-4-yl)-4-pyridinecarboxylic acid, 2-(6-chloro-2-naphthalenyl)-6-(4-chlorophenyl)-4-pyridinecarboxylic acid, 2-(4-bromophenyl)-6-[4-(phenylthio)phenyl]-4-pyridinecarboxylic acid, 2-(4-chlorophenyl)-6-[4-(4-fluorophenyl)phenyl]-4-pyridinecarboxylic acid, 2-(1,1'-biphenyl)-4-yl-6-(4-bromophenyl)-4-pyridinecarboxylic acid, and 2-(4-bromophenyl)-6-(2-naphthalenyl)-4-pyridinecarboxylic acid.

7. A compound of claim 2 selected from the group consisting of

2-[1,1'-biphenyl]-4-yl-6-(4-chlorophenyl)-4-pyridinecarboxylic acid, 2-(4-chlorophenyl)-6-(2-naphthalenyl)-4-pyridinecarboxylic acid, 2-(4-chlorophenyl)-6-(4-phenoxyphenyl-4-pyridinecarboxylic acid, 2-(4-chlorophenyl)-6-[4-(2-phenylthio)phenyl]-4-pyridinecarboxylic acid, 2-(4-methylphenyl)6-(2-naphthalenyl)4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(4-chlorophenyl)-6-(4-fluorophenyl)-3-methyl-4-pyridinecarboxylic acid,
2-(1,1'-biphenyl)-4-yl-6-(4-bromophenyl)-4-pyridinecarboxylic acid and,
2-(4-bromophenyl)-6-(2-naphthalenyl)-4-pyridinecarboxylic acid.

8. A pharmaceutical composition of claim 3, wherein the compound of the Formula II is selected from the group consisting of
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(4-phenoxyphenyl-4-pyridinecarboxylic acid,
2-(4-chlorophenyl)-6-[4-(2-phenylthio)phenyl]-4-pyridinecarboxylic acid,
2-(4-methylphenyl)-6-(2-naphthalenyl)-4-pyridinecarboxylic acid,
2-(4-chlorophenyl)-6-(4'-fluoro-[1,1'-biphenyl]-4-yl)-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(1,1'-biphenyl)-4-yl-6-(4-bromophenyl)-4-pyridinecarboxylic acid and,
2-(4-bromophenyl)-6-(2-naphthalenyl)-4-pyridinecarboxylic acid.

9. A method of claim 1 wherein the compound of the Formula II is selected from the group consisting of
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(4-phenoxyphenyl-4-pyridinecarboxylic acid,
2-(4-chlorophenyl)-6-[4-(phenylthio)phenyl]-4-pyridine-carboxylic acid,
2-(4-methylphenyl)-6-(2-naphthalenyl)-4-pyridinecarboxylic acid,
2-(4-chlorophenyl)-6-(4'-fluoro-[1,1'-biphenyl]-4yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(4-chlorophenyl)-6-(4-fluorophenyl)-3-methyl-4-pyridinecarboxylic acid,
2-(1,1'-biphenyl)-4-yl-6-(4-bromophenyl)-4-pyridinecarboxylic acid, and
2-(4-bromophenyl)-6-(2-naphthalenyl)-4-pyridinecarboxylic acid.

10. A pharmaceutical composition of claim 5, wherein the compound of the Formula II is selected from the group consisting of
2-[1,1'-biphenyl]-4-yl-6-(4-chlorophenyl)-4-pyridinecarboxylic acid,
2-(4-chlorophenyl)-6-(2-naphthalenyl)-4-pyridinecarboxylic acid,
2-(4-chlorophenyl)-6-(4-phenoxyphenyl-4-pyridinecarboxylic acid,
2-(4-chlorophenyl)-6-[4-(2-phenylthio)phenyl]-4-pyridinecarboxylic acid,
2-(4-methylphenyl)-6-(2-naphthalenyl)-4-pyridinecarboxylic acid,
2-(4-chlorophenyl)-6-(4'-fluoro-[1,1'-biphenyl]-4-yl)-4-pyridinecarboxylic acid,
2-(4-chlorophenyl)-6-(2-fluoro-[1,1'-biphenyl]-4-yl)-4-pyridinecarboxylic acid,
2-(6-chloro-2-naphthalenyl)-6-(4-chlorophenyl)-4-pyridinecarboxylic acid,
2-(4-bromophenyl)-6-[4-(phenylthio)phenyl]-4-pyridinecarboxylic acid,
2-(4-chlorophenyl)-6-[4-(4-fluorophenoxy)phenyl]-4-pyridinecarboxylic acid,
2-(1,1'-biphenyl)-4-yl-6-(4-bromophenyl)-4-pyridinecarboxylic acid and,
2-(4-bromophenyl)-6-(2-naphthalenyl)-4-pyridinecarboxylic acid.

* * * * *

UNITED STATES PATENT OFFICE
CERTIFICATE OF CORRECTION

Patent No. 4,474,791          Dated  2 October 1984

Inventor(s) Louis L. Skaletzky

It is certified that error appears in the above-identified patent and that said Letters Patent are hereby corrected as shown below:

Column 4, line 27, "[2-[1,1'-" should read -- 2-[1,1'- --.
Column 9, line 60, "nahthalenyl;" should read -- naphthalenyl; --.
Column 10, line 52, "[4-(4-fluorophenyl)phenyl" should read --[4-(4-fluorophenoxy)phenyl --.
Column 12, line 9, "-4yl-4-" should read -- -4-yl-4- --.

Signed and Sealed this

Fifteenth Day of October 1985

[SEAL]

Attest:

DONALD J. QUIGG

*Attesting Officer*          *Commissioner of Patents and Trademarks—Designate*